US00PP33162P3

(12) United States Plant Patent
Klettke

(10) Patent No.: US PP33,162 P3
(45) Date of Patent: Jun. 15, 2021

(54) HEMP PLANT NAMED 'EIGHTY EIGHT'

(50) Latin Name: ***Cannabis* hybrid**
Varietal Denomination: Eighty Eight

(71) Applicant: Jeremy Klettke, Bend, OR (US)

(72) Inventor: Jeremy Klettke, Bend, OR (US)

( * ) Notice: Subject to any disclaimer, the term of this patent is extended or adjusted under 35 U.S.C. 154(b) by 0 days.

(21) Appl. No.: 16/602,563

(22) Filed: Oct. 30, 2019

(65) Prior Publication Data

US 2021/0136974 P1 May 6, 2021

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/12; A01H 5/00; A01H 6/28; A61K 36/185
See application file for complete search history.

(56) References Cited

PUBLICATIONS

Allbud Oracle Strain 2020, retrieved from the Internet at May 4, 2020, retrieved from the Internet at https://www.allbud.com/marijuana-strains/hybrid/oracle, 4 pp. (Year: 2020).*
Oklahoma Department of Agriculture Food and Forestry 2019, retrieved on Apr. 30, 2020, retrieved from the Internet at http://ag.ok.gov/cps/CertifiedHempSeedList.pdf, 7 pp. (Year: 2019).*
Davis Herb Farms, "Michigan *Cannabis* Expo Ad," made available on Oct. 4, 2019, 1 page.
Davis Herb Farms, "Ohio Hemp Summit Brochure Ad," made available on Aug. 30, 2019, 1 page.
Davis Herb Farms, (2019). "CBD Rich Industrial Hemp Seed Ad," Grow Magazine Quarter PG, made available on Oct. 16, 2019, 1 page.

* cited by examiner

*Primary Examiner* — June Hwu
(74) *Attorney, Agent, or Firm* — Morrison & Foerster LLP

(57) ABSTRACT

A new and distinct cultivar of hemp (*Cannabis*) named 'Eighty Eight' is disclosed, characterized by a 31:1 median ratio of Cannabidiol (CBD) to Tetrahydrocannabinol (THC) at time of harvest, green hollow stem with purple vertical striping, consistently purple petiole on mature leaves, a Myrcene and Limonene dominant terpene profile, high mildew resistance, and low hermaphroditic potential.

5 Drawing Sheets

FIELD OF THE INVENTION

Botanical classification: *Cannabis* hybrid.
Variety denomination: 'Eighty Eight'.

BACKGROUND OF THE INVENTION

The present invention comprises a new and distinct hemp cultivar, hereinafter referred to by the cultivar name, 'Eighty Eight'. It is noted that "hemp" is a term used to describe varieties of *Cannabis* that contain 0.3% or less Tetrahydrocannabinol (THC) content by dry weight.

The inventor, Jeremy Klettke, discovered the new cultivar of distinct lineage as a result of crossing two stabilized open source (unpatented) parents, hybridized from the species *Cannabis sativa* L. and *Cannabis indica*. More specifically, 'Eighty Eight' was discovered through a series of outdoor field trials carried out in 2016, 2017, and 2018, combined with a number of parallel indoor pollination projects at Mr. Klettke's breeding facility in LaPine, Oreg. 'Eighty Eight' was the result of working with more than 4,000 individual variations of this hybrid.

Further developed in a closed environment breeding program, carried out indoors, 'Eighty Eight' is characterized as an average yielding cultivar for Cannabidiol (CBD) production containing very low quantities of THC, Cannabigerol (CBG), Resorcinol, 2-(3,7-dimethyl-2,6-octadienyl)-5-pentyl, Cannabichromenic Acid (CBC-A), 5-hydroxy-2methyl-2-(4-methylpent-3-enyl)-7-pentyl-chromene-6-carboxylic acid. 'Eighty Eight' also contains a Myrcene and Limonene dominant terpene profile.

Asexual reproduction of the new cultivar has been done by stem propagation performed at Mr. Klettke's breeding facility in LaPine, Oreg. The unique features of this cultivar are stable and reproduced true to type through successive generations. This is a cultivar bred for plant resin production, containing quantifiable and extractable amounts of CBD, CBG, CBC, Myrcene, and Limonene, with very low accompanying quantities of any psychoactive compounds such as THC, Tetrahydrocannabivarin (THCV), and Cannabinol (CBN).

SUMMARY OF THE INVENTION

In the following description, color references are made to The Royal Horticultural Society Colour Chart (R.H.S. Colour Chart), $6^{th}$ edition, 2015, except where general terms of ordinary dictionary significance are used.

The term "cultivar" is used herein interchangeably with "variety" "strain," and/or "clone."

The cultivar 'Eighty Eight' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Eighty Eight'. These characteristics in combination distinguish 'Eighty Eight' as a new and distinct hemp cultivar:

1. This plant is stable and quick growing.
2. This plant is able to grow in a number of microclimates and bioregions.
3. This plant is resistant to powdery mildew (*Podosphaera xanthii*), grey mold or *Botrytis* (*Botrytis cinerea*), and white mold (*Sclerotinia sclerotiorum*).
4. This plant contains measurable quantities of non-psychoactive compounds such as CBD, CBG, CBC, and Terpenes such as Myrcene and Limonene, and contains low quantities of THC or any other intoxicating compound, with a median CBD to THC ratio of 31:1 at time of harvest. The range of cannabinoids by percentage weight is 7-12%. Specifically, the range of CBD by percentage weight is 7-9%, the range of CBG by percentage weight is 0.09-0.5%, the range of CBC by percentage weight is 0.07-0.1%, and the range of THC by percentage weight is 0.2-0.3%.
5. This plant contains significantly higher quantities of minor cannabinoids and terpenes than either of its parents. Specifically, this plant has higher quantities of beta-Myrcene, beta-Carophyllene, Ocimene Isomer II, alpha-Pinene, beta-Pinene, alpha-Humulene, alpha-Basabolol, Limonene, and endo-fenchyl alcohol when compared to its parents. As determined by liquid chromatography, the range percentages by weight of cannabinoids are 7.8-12.1%, and the range percentages by weight of terpenes are 0.75-3.5%.
6. This plant has low hermaphroditic potential.
7. This plant naturally breaks apically dominant growth providing greater yield potential.

BRIEF DESCRIPTION OF THE DRAWINGS

Colors in the photographs may appear different from the color values that appear in the detailed botanical description which more accurately describe the new cultivar.

The photographs were taken using conventional techniques and, although colors may appear different from actual colors due to light reflectance, it is as accurate as possible by conventional photographic techniques.

DETAILED DESCRIPTION OF THE PREFERRED EMBODIMENTS

Figure 1:
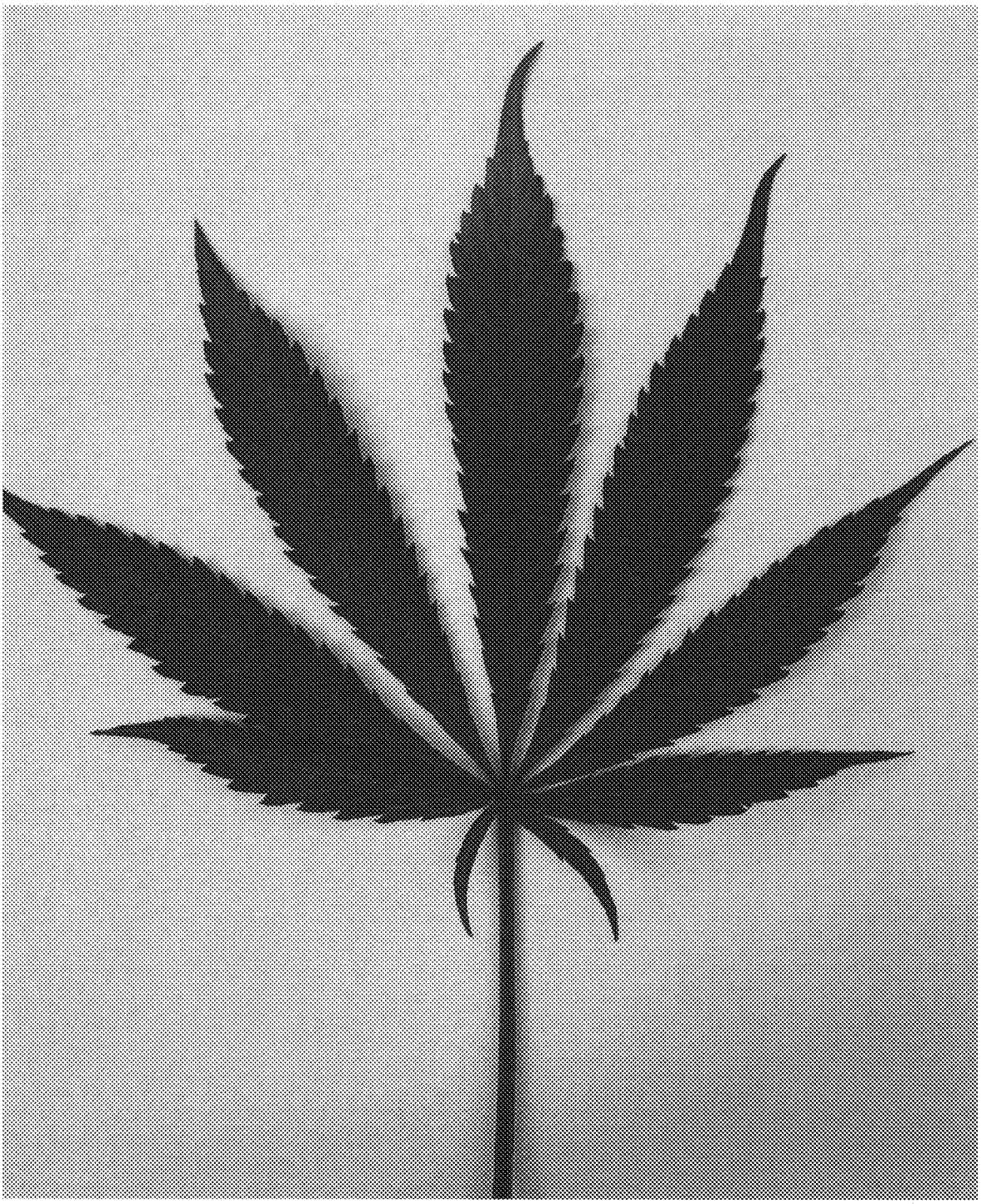
FIG. 1 is a top view of a plant of 'Eighty Eight', showing a developed water leaf.
Figure 2:
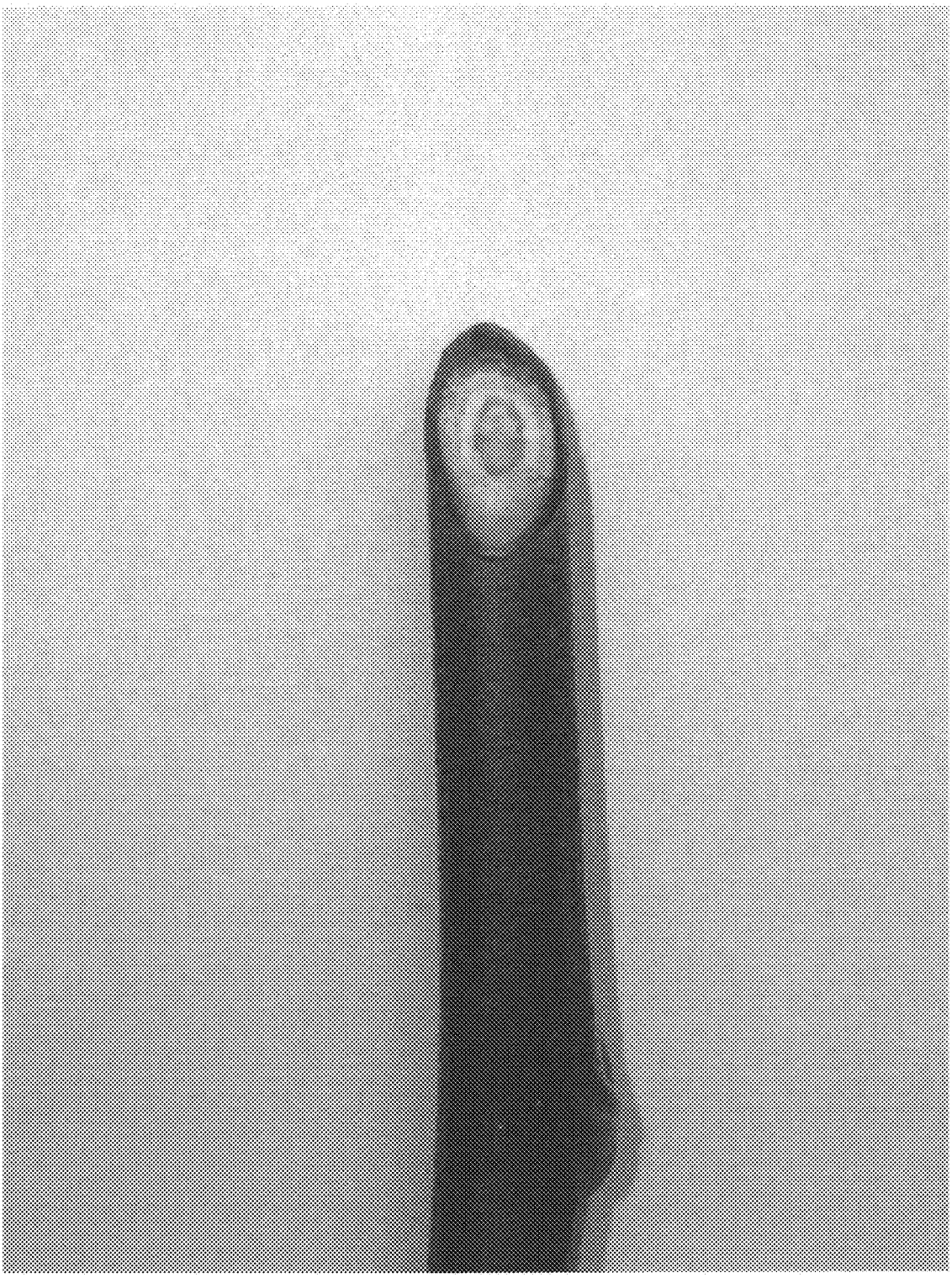
FIG. 2 is a side view of a plant of 'Eighty Eight', showing a cross-section of a cut stem.
Figure 3:
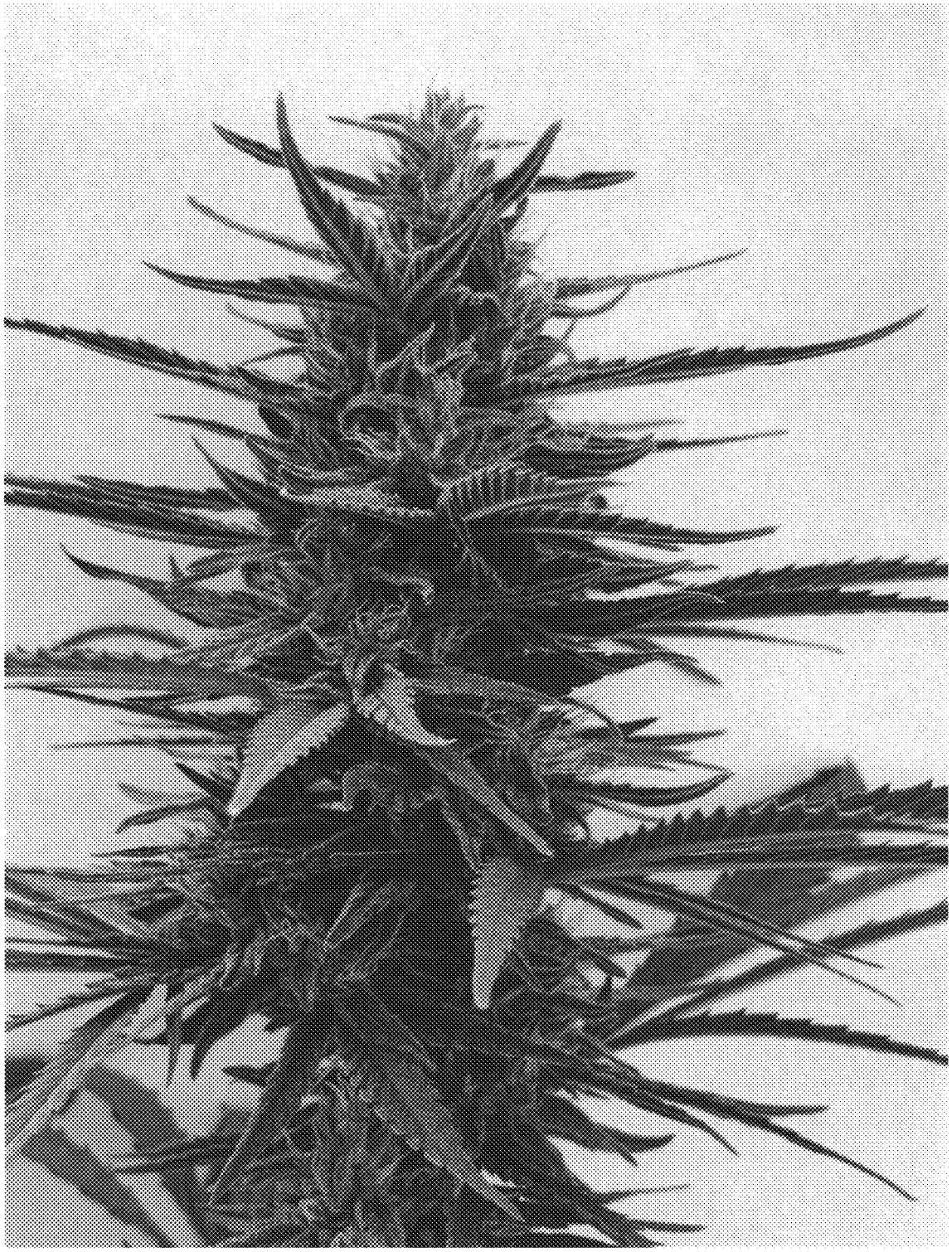
FIG. 3 is a side view of a plant of 'Eighty Eight', showing an immature, partially developed flower.
Figure 4:
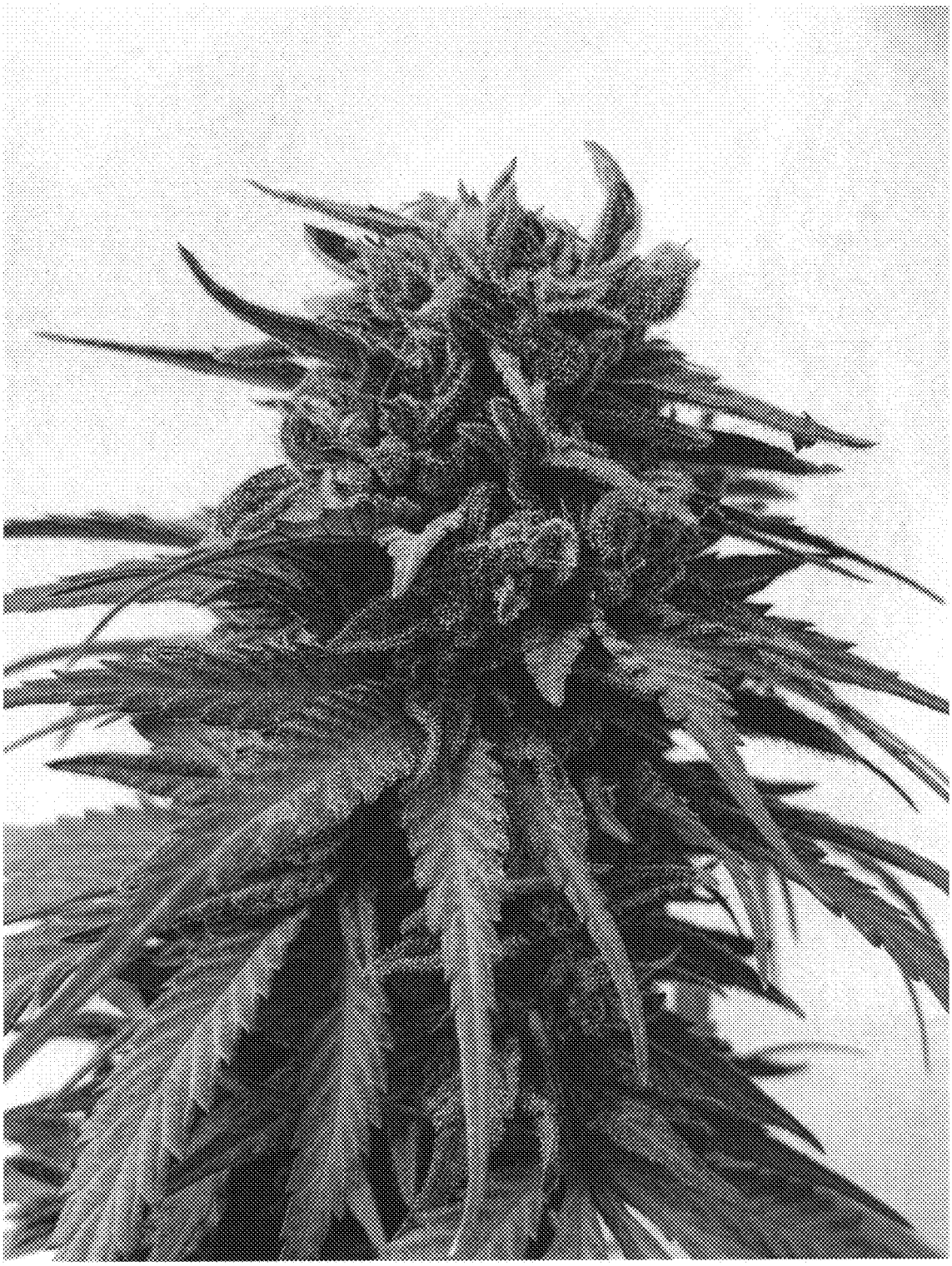
FIG. 4 is a side view of a plant of 'Eighty Eight', showing a mature, developed flower.
Figure 5:
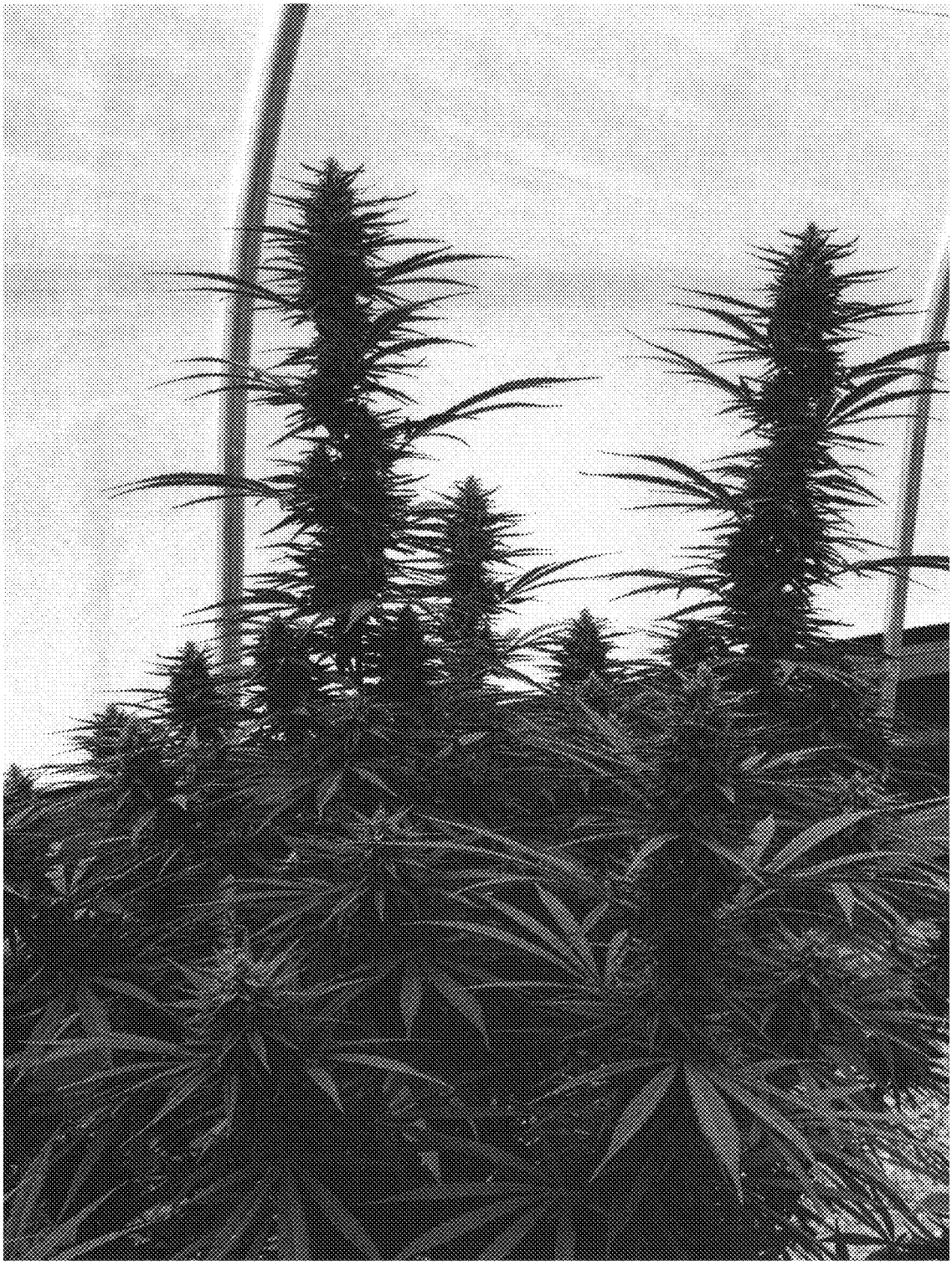
FIG. 5 is a side view of a plant of 'Eighty Eight', showing a whole, mature plant.

This invention relates to a new hemp plant hybrid of *Cannabis sativa* L. and *Cannabis indica* named 'Eighty Eight'. 'Eighty Eight' is a plant bred for indoor and outdoor production of plant resin containing measurable quantities of non-psychoactive compounds such as CBD, CBG, CBC, Terpenes such as Myrcene and Limonene, and low quantities of THC or any other intoxicating compound. The present plant was developed over 3.5 years at Mr. Klettke's breeding facility in LaPine, Oreg., using parents selected from open source unstabilized dioecious seed and propagated cuttings. The plant can be grown in most climates through a normal summer growing season from 30-50 degrees of latitude either North or South of the equator. Although this plant is primarily dependent on the photoperiod for flowering, it can be grown throughout a large part of the year in latitudes within 15 degrees of the equator.

Parentage:

*Seed.*—Unnamed *Cannabis* hybrid 'Oracle' x 'Otto II' #254 x 'American Feral' #96.

*Pollen.*—Unnamed *Cannabis* hybrid 'Oracle' x 'Otto II' #259.

The parent plants of 'Eighty Eight' consist of a mother developed from the crossing of an elite, open source clone named 'Oracle' crossed with an unstabilized open source wild male plant from the Midwestern United States referred to as 'American Feral'. The father is a selection made by the inventor from a developed but unstabilized open source hemp seed variety named 'Otto II'. 'Oracle' is a stable resin producing female with a CBD to THC ratio of 20:1 and has been available in limited circles of *Cannabis* cultivators and breeders.

'Oracle' is a short growing bushy plant with 1-1.5 inch internodal spacing with moderately broad leaf structure. 'American Feral' is a developed line created at Mr. Klettke's breeding facility and was selected from an indoor closed pollination project done in Mr. Klettke's breeding facility in 2017, which included pollen selected from 5 male plants and 96 different female plants. The 101 selections included in this closed pollination project were chosen from the expressions and analytics from 423 wild seeds collected in the Midwestern United States in 2015 and grown outdoors in a field trial in Oregon in 2016. 'Otto II' was developed and released in seed form as a CBD producing hemp cultivar for outdoor production. 'Otto II' contains small but measurable amounts of terpenes and very little THC, with ratios of CBD to THC ranging from 15:1 through 25:1

The claimed plant 'Eighty Eight' has been stabilized and has a median CBD to THC ratio of 31:1, with analytics consistently remaining below a total threshold of 0.3% THC. 'Eighty Eight' also contains significantly higher quantities of minor cannabinoids and terpenes (predominately Myrcene and Limonene) than either of its parents and has been bred to a point of stability which helps the plant avoid hermaphroditic potential. 'Eighty Eight' has a longer internodal spacing than its mother plant and a shorter internodal spacing than its father plant.

TABLE I

| | |
|---|---|
| LATIN NAME OF THE FAMILY, GENUS AND SPECIES | *Cannabis* hybrid |
| VARIETY DENOMINATION | 'Eighty Eight' |
| MARKET CLASS | Hemp |
| PROPAGATION | Typically propagated asexually via stem cuttings and F1 rootstock. Cloning is performed in a propagation chamber with low par reduced spectrum lighting. The |

TABLE I-continued

| LATIN NAME OF THE FAMILY, GENUS AND SPECIES | *Cannabis* hybrid |
|---|---|
| | propagation chamber has reduced environmental variablity to maintain a relative humidity at or about 75% and a constant temperature of 72 degrees Fahrenheit. |
| PLANT DESCRIPTION | Branching, bush-like structure with multiple terminal branches. The natural height of the plant at annual harvest (maturity) is 4-5 feet, and the width is 5-6 feet. The plant is primarily self supporting through its life cycle and will not require trellising. |
| STEM DESCRIPTION | Hollow ribbed stem with some purple striping on the more mature woody parts. Stem thickness is medium, stem depth of ribbing is medium, and stem pith in cross-section is medium. Shoots and stems have a rough sand-paper-like feel due primarily to sessile glands on the leaf surface. Young shoots are wintergreen in color (RHS 128A) changing to darker green (RHS 132C) and finally to purple (RHS N74A). |
| BUD DESCRIPTION | Early flower development and heavy resin production in early flowering, stigma that are primarily white (RHS N155C) in color with some orange hues (RHS 158C), uniform 1.618:1 calyx braiding or stacking (represents the "Golden Ratio" or "Phi", meaning the symmetry of the calyx braiding is identical). Finished buds or pistillate inflorescence range in size from 12-18 inches in length on the primary branches with broken internodal buds continuing down the branches for 3-4 feet toward the base of the plant with increased sparsity. Finished buds range in color from light green (RHS 140C) to purple (RHS N74A). |
| LEAF DESCRIPTION | Each leaf is compound and contains either 7 or 9 leaflets with very unique double serration at the leaf edges. The leaflets are semi-narrow with little separation at the base and no overlap. The average leaf length is 6 inches, the central leaflet average length is 7 inches, and the central leaflet average width is 0.75 inch. The leaf surface texture is rough on the top due to stiff hairs and both sides are covered with sessile glands. The leaf fragrance is earthy with a hint of sweetness. The upper leaf surface color is strong green (RHS 132C) and the lower leaf surface color is strong yellow green (RHS 142A). The venation pattern is primarily palmate, and serrated leaflets express unique double serration with a split vein to each serrated tip. Branching is symmetrical with opposing internodes and leaves firmly attached to the meristem. The petiole has an average length of 1.6 inches and an average diameter of 4 mm. The petiole trichome type is a sessile gland with limited to no capitate head. The petiole intensity of anthocyanin is medium, and the petiole color is brilliant yellowish green (RHS 134C). The stipule is 1/16-1/8 of an inch in size, and narrow and needle-like in shape. The stipule contains no visible trichomes. The stipule color is brilliant yellow green (RHS 142B). |
| FLOWER DESCRIPTION | The flowers when finished are large at 2-2.5 inches in diameter on average, covered in trichomes or resin glands and of moderate density, making the plant better at shedding water. As a result of the flower structure, the plant has naturally above average mildew resistance. The finished flower is highly resinous and pungently aromatic. The appearance of the dried flower is sparkling with trichomes. At maturity, the leafy parts of the flower (primarily sugar leaves) remain green at the center with mild purple hues at the leaf tips. The pistillate inflorescence are purple (RHS 186A) and the stigma remain orange and white until maturity. The immature stigma color is pale yellow green (RHS 149D), and the mature stigma color is moderate orange yellow (RHS 164B). The average length of the stigma is 4 mm. The flowering season is May through October. The average bract size is 1-1.5 cm, and the bract quantity per flower is several dozen. The bract shape is oval, and the bract trichome type is sessile. The bract color is strong yellowish green (RHS 141C). The average bracteole size is 2-3 mm, and the bracteole quantity per flower is 4-6. The bracteole has a sessile trichome type. The bracteole shape is arrow-like, and the bracteole color is brilliant green (RHS 128A). The average sugar leaf size is 10 cm. The sugar leaf has both glandular and non-glandular trichome types. The sugar leaf color is strong yellowish green (RHS 141C). |
| FRUIT DESCRIPTION | The fruit type is pistillate inflorescence. The fruit shape is a short and fat pear shape. The average size of the fruit is 4.5 inches in diameter and 6 inches in length. The fruit color is deep purplish red (RHS 61A). |
| ROOT DESCRIPTION | Short taproot from seed that is generally not deeper than 30 cm at maturity. There are dense subsurface lateral roots spreading out to 70 cm from the base of the plant. |
| SEED DESCRIPTION | The seeds are 2-2.5 mm long with a slightly oval shape that has a depression at one end and a rounded point at the opposite end. The seeds are dark purple to black in color without visible surface veins. The seed color of testa is greyish yellow green (RHS 198A), and seed marbling is medium. The average weight per 1000 seeds is low (less than 10 grams). |
| FRAGRANCE/TASTE | The finished pistillate inflorescences have a terpene profile containing the strong smell of lemons with general citrus undertones. The stems when rubbed produce a similar citrus aroma. |
| GROWTH HABIT | Annual, dioecious, erect herb. Naturally bushy and branching multi-top plant with an average internodal spacing of 2.25 inches. |
| DISEASE RESISTANCE | Naturally pest and disease resistant. Bred from pest, pathogen, and virus free mother stock to reduce the potential for any predisposition for a virus or pathogen to influence the genetic material. Also contains minor quantities of the terpene Farnesene, which has been shown in trials to be a natural pesticide. The plant has shown resistance to the pests fall armyworm (*Spodoptera ornithogalli*), two spotted spider mite (*Tetranychus urticae*), and broad mite (*Polyphagotarsonemus latus*). The plant is resistant to most common molds, including *Botrytis cinerea*, and powdery mildews, such as *Podosphaera xanthii*. In addition, the plant has shown some resistance to Hyphomycetes such as *Fusarium* spp. |
| PRODUCTIVITY | The plant is grown annually in a moderate climate with a growing season of 5 to 6 months. Over an average growing summer, the plant will yield 1-2 lbs. of dried plant material. Average time from planting to harvest is 4.5-5.5 months. The shipping quality is high. The market use is for oil production and smokable flower production. The storage life is 3-6 months depending on storage climate. |
| TEMPERATURE TOLERANCE | Frost resistance down to 30° Fahrenheit as a young sapling. Frost resistance down to 22° Fahrenheit as a mature flowering plant |
| GROWTH CYCLE | Outdoor: Annual from March to October. Indoor: Photoperiod dependent vegetative cycle with an approximate 60 day flowering cycle. |

COMPARISON TO RELATED KNOWN CULTIVAR

'Eighty Eight' is distinguished from 'Painted Lady' (U.S. Plant patent application Ser. No. 16/602,561) in that the plant of 'Eighty Eight' is slightly shorter in height than the plant of 'Painted Lady'. Further, the flowers of 'Eighty Eight' have internode spacing that is closer together, which provides the flowers with a shorter and more compact appearance than the flowers of 'Painted Lady'. In addition, the overall color palette of 'Eighty Eight' is darker than the overall color palette of 'Painted Lady'.

What is claimed is:

1. A new and distinct cultivar of hemp plant named 'Eighty Eight' as illustrated and described.

* * * * *